(12) United States Patent
Suzuki et al.

(10) Patent No.: US 6,365,771 B1
(45) Date of Patent: Apr. 2, 2002

(54) ALICYCLIC COMPOUND AND CURABLE RESIN COMPOSITION

(75) Inventors: Hideo Suzuki; Takayasu Nihira, both of Funabashi; Shinichiro Takigawa, Tokyo, all of (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 09/786,443

(22) PCT Filed: Sep. 10, 1999

(86) PCT No.: PCT/JP99/04929

§ 371 Date: Mar. 14, 2001

§ 102(e) Date: Mar. 14, 2001

(87) PCT Pub. No.: WO00/15591

PCT Pub. Date: Mar. 23, 2000

(30) Foreign Application Priority Data

| Sep. 11, 1998 | (JP) | ............................................ | 10-258333 |
| Mar. 23, 1999 | (JP) | ............................................ | 11-078394 |
| Jul. 22, 1999 | (JP) | ............................................ | 11-207383 |

(51) Int. Cl.[7] .......................... C07C 69/52; C07C 67/30; C07C 41/00
(52) U.S. Cl. ....................... 560/220; 560/205; 560/211; 568/665; 568/664; 568/667
(58) Field of Search ................................ 560/220, 205; 560/211; 568/665, 664, 667

(56) References Cited

FOREIGN PATENT DOCUMENTS

| JP | A 57-82330 | 5/1982 |
| JP | A 60-156683 | 8/1985 |
| JP | A 1-121370 | 5/1989 |
| JP | A 2-115205 | 4/1990 |
| JP | A 5-265212 | 10/1993 |
| JP | A 7-206740 | 8/1995 |
| JP | A 7-206741 | 8/1995 |
| JP | A 8-82925 | 3/1996 |
| JP | A 8-206741 | 8/1996 |
| JP | A 10-25262 | 1/1998 |

Primary Examiner—Samuel Barts
Assistant Examiner—Elvis O. Price
(74) Attorney, Agent, or Firm—Oliff & Berridge, PLC

(57) ABSTRACT

Decane compound or decene compound shown in the formula [1] below

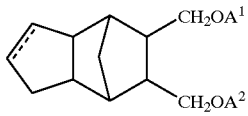

[1]

wherein $A^1$ and $A^2$ are independently hydrogen or (meth)acryloyl group or 2-vinyloxyethyl group; and the dotted line is single bond or double bond with the proviso that $A^1$ and $A^2$ are not hydrogen at the same time; and curable resin composition containing said compound therein.

The compound are suitable as the photo-monomer for resist raw materials because of high clarity at short wavelength ultraviolet light, dry etching resistance, adhesive property for the substrate and high solubility in alkaline developing solution in addition to high sensitivity and greater resolution; as the monomer for optic raw materials and disk overcoat materials because of high clarity, low birefringence and low water absorption rate; and as the monomer for the coating raw materials such as EB curable coating raw materials because of high reactivity, high wear characteristics and water resistance.

6 Claims, No Drawings

ALICYCLIC COMPOUND AND CURABLE RESIN COMPOSITION

This is the National Phase Application of PCT/JP99/04929, filed Sep. 10, 1999.

TECHNICAL FIELD

The present invention relates to tricyclo[5.2.1.0$^{2,6}$]decane compound or tricyclo[5.2.1.0$^{2,6}$]dece-3-ene compound shown in the formula [1] below and the curable resin composition containing said compound described above

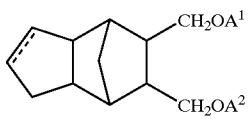
[1]

wherein A$^1$ and A$^2$ are independently hydrogen; or acryloyl group or methacryloyl group shown in the formula [2] below

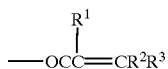
[2]

wherein R$^1$ is hydrogen or C$_1$–C$_4$ alkyl; and R$^2$ and R$^3$ are independently hydrogen or C$_1$–C$_{10}$ alkyl; or 2-vinyloxyethyl group shown in the formula [3] below

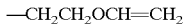
[3]

wherein the dotted line is a single bond or double bond with the proviso that A$^1$ and A$^2$ are not hydrogen at the same time.

The compound in the present invention relates to the monomer used in the field of pattern style materials suitable for the lithography with active light radiation such as ultraviolet rays, far ultraviolet rays, electron rays, ion beam and X-rays, and the curable resin composition containing said monomer. Further, the compound in the present invention relates to the monomer raw materials agent, optical materials and adhesive agents by having reactive ethylenic unsaturated groups within the molecule as well as the highly heat resistant tricyclodecane structure, and the curable resin composition containing said monomer.

BACKGROUND ART

Up to now, the compound shown in the formula below is known as the compound having more than one unsaturated groups in the molecule of alicyclic compound or as the main component of monomer raw materials for the overcoat agent composition for optical disk (JP Laid-Open Hei 1-121370).

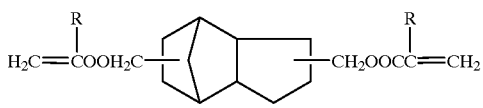

The resin composition for optical raw materials consisting of the compound shown in the formula below as the main component of said composition is also known (JP Laid-Open Hei 2-115205).

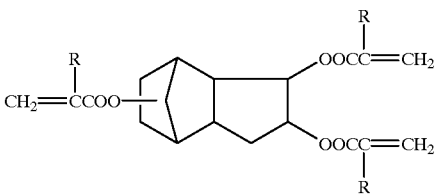

In addition, the inventor of the present invention had already filed the patent application relating to tricyclo[5.2.1.0$^{2,6}$]dece-3-ene-8,9-dicarboxylic acid diallyl (abbreviated as TDEA) shown in the formula below (JP Laid-Open Sho 60-156683).

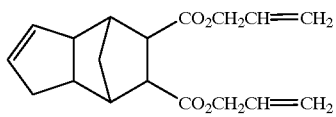

However, polyester using TDEA have shown low reactivity of polymerization of allyl group and therefore the satisfactory result was not obtained in using said resin composition for acrylic optical raw materials.

Copolymer having adamantylmethacrylate unit of alicyclic polymer as a polymer compound with the clarity at 193 nm wavelength and yet with dry etching resistance [Takechi, S. et al., Journal of Photopolymer Science and Technology, 5 (3):439–446 (1992); and JP Laid-Open Hei 5-265212], poly (norbornylmethacrylate) [Endo, M. et al., Proceedings of IEDM], CA14-18, San Francisco (1992)] or copolymer having poly (isobornylmethacrylate) unit [Wallraff, G. M. et al., Journal of Vacuum Science and Technology, B11 (6):2783–2788 (1993)], and copolymer having poly (menthylmethacrylate) unit [JP Laid-Open Hei 8-82925] have been proposed.

On the other hand, aromatic derivatives such as 2,2-bis (4-(2-vinyloxy)ethoxy)phenyl)propane shown in the formula below

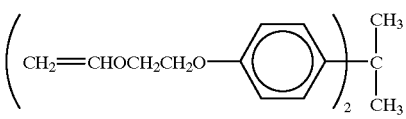

or aliphatic vinylether derivatives such as bis(2-vinyloxyethyl)ether, 1,2-bis[(2-vinyloxy)ethoxy]ethane and the like are well known as vinylether derivatives heretofore [Chemistry of Materials, 6 (10): 1854–1860 (1994)].

However, alicyclic derivatives having vinyloxyethyloxymethyl group at 8 and 9 positions of tricyclo[5.2.1.0$^{2,6}$]dece-3-ene or tricyclo[5.2.1.0$^{2,6}$]decane were not known at all.

The existing art described above do not contain residues which can manifest the difference in solubility before and after the light exposure within the residue unit of alicyclic group (adamantyl, norbornyl, isobornyl or menthyl) which result in dry etching resistance, and therefore the use as the resin component for the resist by preparing copolymer with co-monomer such as t-butylmethacrylate or tetrahydropyranylmethacrylate which can manifest the difference in solubility has been employed in the pertinent art heretofore. However, the patterning has been employed in the pertinent art heretofore. However, the patterning requires about 30–50% co-monomer content, and as a result, the effect of dry etching resistance due to alicyclic group structure was drastically reduced and their utility have been questionable.

The existing art heretofore in use do not have any polar site within the molecules and therefore adhesion to the silicon substrate is poor. In addition, sensitivity is low because of low solubility in alkaline developing aqueous solution, and furthermore, there is a shortcoming of dregs left in the developing solution in all likelihood.

DISCLOSURE OF INVENTION

The object of the present invention is to prepare the novel alicyclic compound suitable as photo-monomer for the resist raw materials by having high clarity at short wavelength ultraviolet light and by excelling in dry etching resistance due to tricyclo ring structure, and by showing adhesion for the substrate and high solubility in alkaline developing solution in addition to high sensitivity and greater resolution, as monomer for optic raw materials and disk overcoat materials by having high clarity, low birefringence and low water absorption rate, and as monomer for the coating raw materials such as EB curable coating by having high reactivity, high wear characteristics and water resistance and to provide the curable resin composition containing said compound.

The present inventors made the utmost effort in solving the problems described above. The present invention have been completed after the selection of tricyclodecanyl group as an alicyclic group in order to obtain high clarity and high dry etching resistance and the introduction of hydroxymethyl group as a polar substituent in order to achieve good adhesion for the substrate and high solubility in alkaline developing solution in addition to high sensitivity and greater resolution.

Thus, the present invention relates to tricyclo[$5.2.1.0^{2,6}$] decane compound or tricyclo[$5.2.1.0^{2,6}$]dece-3-ene compound shown in the formula [1] below

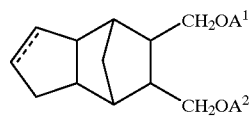

[1]

wherein $A^1$ and $A^2$ are independently hydrogen; or acryloyl group or methacryloyl group shown in the formula [2] below

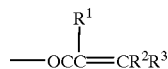

[2]

wherein $R^1$ is hydrogen or $C_1$–$C_4$ alkyl; and $R^2$ and $R^3$ are independently hydrogen or $C_1$–$C_{10}$ alkyl; or 2-vinyloxyethyl group shown in the formula [3] below

—CH$_2$CH$_2$OCH=CH$_2$ [3]

wherein the dotted line is single bond or double bond with the proviso that $A^1$ and $A^2$ are not hydrogen at the same time, and the curable resin composition containing said compound therein.

$C_1$–$C_4$ alkyl group in the definition of $R^1$ is straight or branched alkyl group such as methyl, ethyl, propyl, isopropyl, n-butyl, isobutyl, s-butyl, t-butyl and the like.

$C_1$–$C_{10}$ alkyl group in the definition of $R^2$ and $R^3$ is also straight or branched alkyl group such as 2-ethylbutyl, n-pentyl, isopentyl, 1-methylpentyl, 1,3-dimethylbutyl, n-hexyl, 1-methylhexyl, n-heptyl, isoheptyl, 1-methylheptyl, 3-methylheptyl, n-octyl, 2-ethylhexyl, nonyl, decyl and the like in addition to groups described above.

Following compounds described below may be abbreviated as shown in the left.

DOL: 8,9-bis(hydroxymethyl)tricyclo[$5.2.1.0^{2,6}$]dece-3-ene

DH-DOL: 8,9-bis(hydroxymethyl)tricyclo[$5.2.1.0^{2,6}$]decane

DH-DOLMA: acryloyloxymethyl-9-hydroxymethyltricyclo[$5.2.1.0^{2,6}$]decane

DH-DOLMM: 8-methacryloyloxymethyl-9-hydroxymethyltricyclo[$5.2.1.0^{2,6}$]decane DH-DOLDA: 8,9-bis(acryloyloxymethyl)tricyclo[$5.2.1.0^{2,6}$]decane DH-DOLDM: 8,9-bis(methacryloyloxymethyl)tricyclo[$5.2.1.0^{2,6}$]decane DOLMV: 8(or 9)-hydroxymethyl-9(or 8)-(2-vinyloxyethyl)oxymethyl-tricyclo[$5.2.1.0^{2,6}$]dece-3-ene DH-DOLMV: 8-hydroxymethyl-9-(2-vinyloxyethyl)oxymethyl-tricyclo[$5.2.1.0^{2,6}$]decane DOLVE: 8,9-bis[(2-vinyloxyethyl)oxymethyl]tricyclo[$5.2.1.0^{2,6}$]dece-3-ene DH-DOLVE: 8,9-bis[(2-vinyloxyethyl)oxymethyl]tricyclo[$5.2.1.0^{2,6}$]decane HVE: 2-haloethylvinylether VEC: 2-chloroethylvinylether Alicyclic compounds shown in the formula [1] above of the present invention can be grouped into A)–D) below.

A) 8-(meth)acryloyloxymethyl-9-hydroxymethyltricyclo[$5.2.1.0^{2,6}$]decane compound, or 9-(meth)acryloyloxymethyl-8-hydroxymethyltricyclo[$5.2.1.0^{2,6}$] dece-3-ene compound or 8-(meth)acryloyloxymethyl-9-hydroxymethyltricyclo[$5.2.1.0^{2,6}$]dece-3-ene compound shown in the formula [4a] or [4b] below

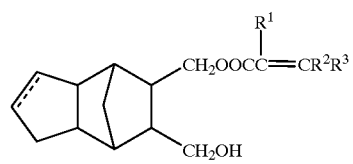

[4a]

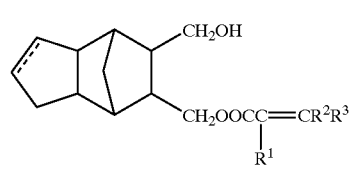

[4b]

wherein $R^1$ is hydrogen or $C_1$–$C_4$ alkyl; $R^2$ and $R^3$ are independently hydrogen or $C_1$–$C_{10}$ alkyl; and the dotted line is single bond or double bond.

B) 8,9-bis((meth)acryloyloxymethyl)tricyclo[$5.2.1.0^{2,6}$] decane compound or 8,9-bis((meth)acryloyloxymethyl) tricyclo[$5.2.1.0^{2,6}$]dece-3-ene compound shown in the formula [5] below

[5]

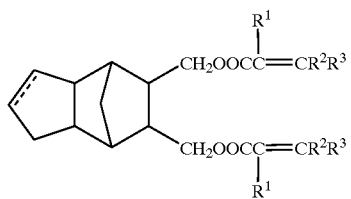

wherein $R^1$ is hydrogen or $C_1$–$C_4$ alkyl; $R^2$ and $R^3$ are independently hydrogen or $C_1$–$C_{10}$ alkyl; and the dotted line is single bond or double bond.

C) 8-hydroxymethyl-9-(2-vinyloxyethyl)oxymethyl-tricyclo[5.2.1.0$^{2,6}$]decane, or 8-hydroxymethyl-9-(2-vinyloxyethyl)oxymethyl-tricyclo[5.2.1.0$^{2,6}$]dece-3-ene or 9-hydroxymethyl-8-(2-vinyloxyethyl)oxymethyl-tricyclo[5.2.1.0$^{2,6}$]dece-3-ene shown in the formula [6a] or [6b] below

[6a]

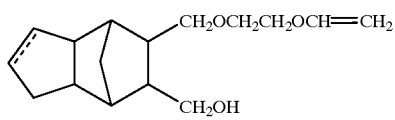

[6b]

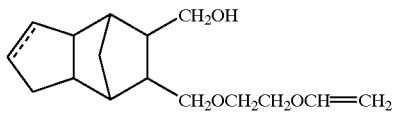

wherein the dotted line is single bond or double bond.

D) 8,9-bis[(2-vinyloxyethyl)oxymethyl]tricyclo[5.2.1.0$^{2,6}$]decane or 8,9-bis[(2-vinyloxyethyl)oxymethyl]tricyclo[5.2.1.0$^{2,6}$]dece-3-ene shown in the formula [7] below

[7]

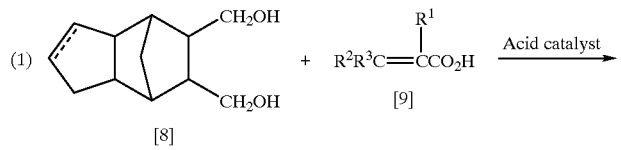

wherein the dotted line is single bond or double bond.

The method of preparation for (meth)acryl compounds shown in the formula [4a] and [4b], and [5] are described in (1)–(3) of the Reaction Scheme I below.

Reaction Scheme I

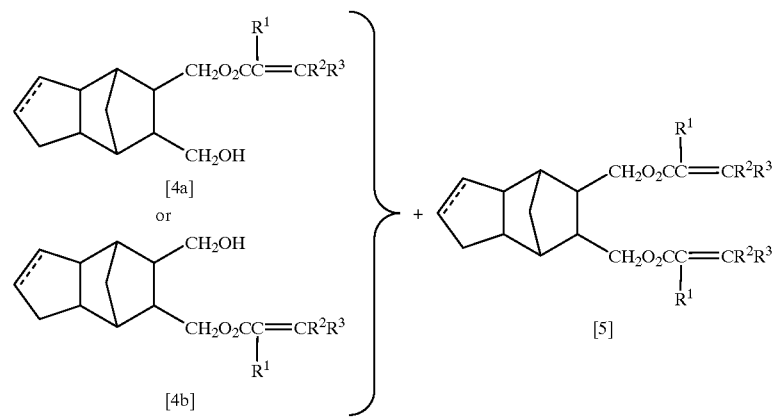

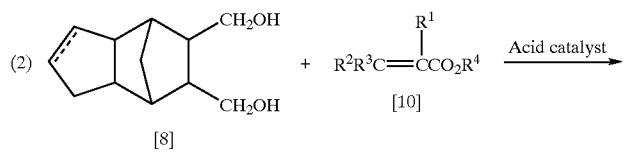

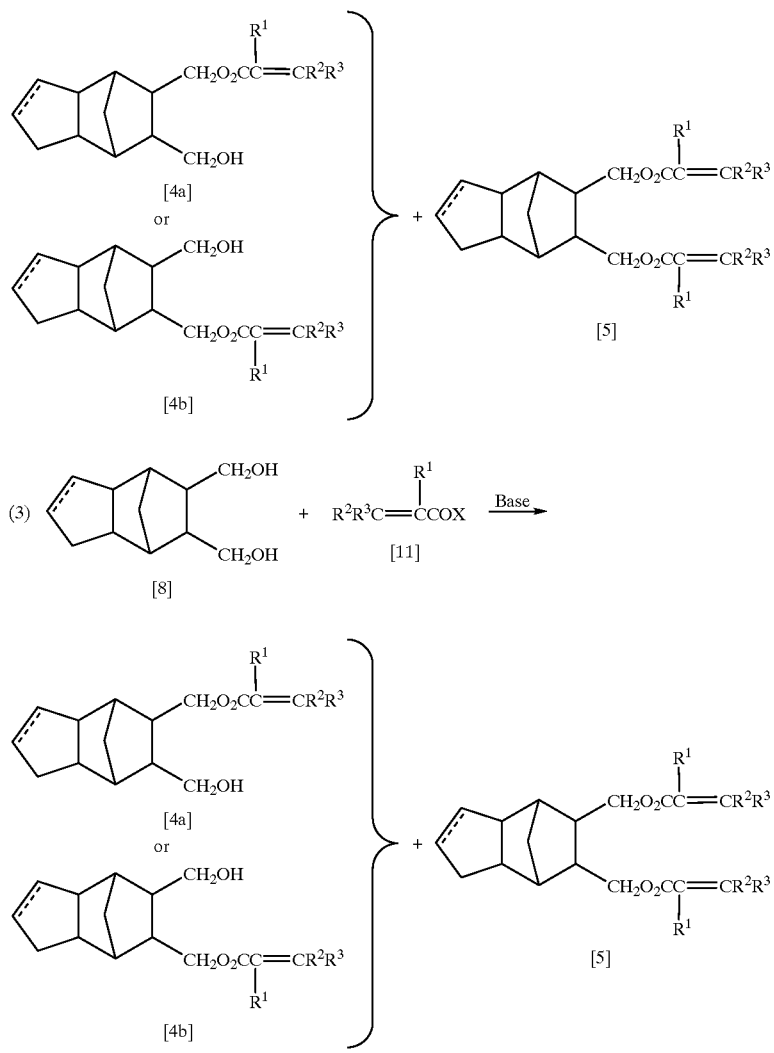

wherein $R^1$, $R^2$, $R^3$ and the dotted line are the same meaning as above; $R^4$ is hydrogen or $C_1$–$C_{10}$ alkyl; and X is halogen.

8,9-bis(hydroxymethyl)tricycto[5.2.1.0$^{2,6}$]dece-3ene (DOL) shown in the formula [8] as a starting raw material can be obtained by the method disclosed in JP Laid-Open Hei 8-206741 as described below.

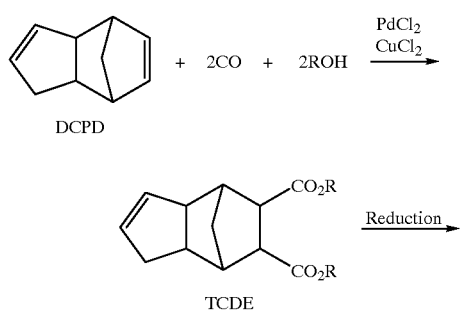

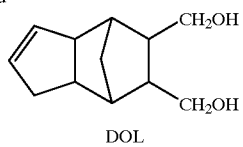

That is to say that 8,9-bis(alkoxycarbonyl)tricyclo[5.2.1.0$^{2,6}$]dece-3-ene (TCDE) can be obtained from the reaction with dicyclopentadiene (DCPD), carbon monoxide and alcohol compound under the existence of ferric chloride with palladium catalyst. DOL can be further obtained by the reduction of this TCDE.

In addition, 8,9-bis(hydroxymethyl)tricyclo[5.2.1.0$^{2,6}$]decane (DH-DOL) can be obtained by the method disclosed in JP Laid-Open Hei 7-206740 by the present inventors described below.

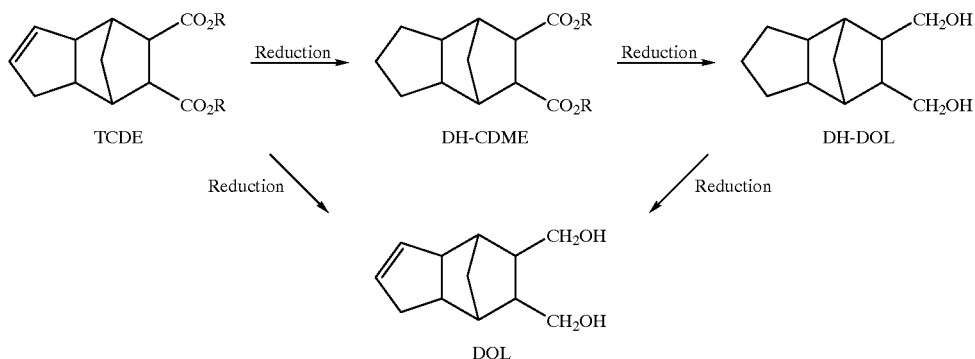

Namely, said compound can be obtained either by the method in which double bond in TCDE is first reduced before the reduction of carbonyl group or by the method in which carbonyl group in TCDE is first reduced and then double bond in DOL thus obtained is reduced.

Further, $R^1$ in (meth)acryl compound shown in the formula [9] or the formula [10] as an other starting raw material is hydrogen or $C_1$–$C_4$ alkyl group, and preferably hydrogen or $C_1$–$C_2$ alkyl group. Moreover, $R^2$, $R^3$ and $R^4$ are hydrogen or $C_1$–$C_{10}$ alkyl group, and preferably hydrogen or $C_1$–$C_5$ alkyl group. Alkyl group in these examples cited are the numbers of carbon atoms corresponding to the examples of alkyl group in the embodiments described above.

Concrete examples of these (meth)acryl compounds are such as acrylic acid, methacrylic acid, tiglic acid, 3,3-dimethylacrylic acid, 2-methyl-2-pentanoic acid, 2-ethyl-2-hexanoic acid and 2-octanoic acid and the like, and $C_1$–$C_{10}$ acrylic acid ester compound thereof such as acrylic acid methyl, acrylic acid ethyl, methacrylic acid methyl, methacrylic acid ethyl, tiglic acid methyl, tiglic acid ethyl, 3,3-dimethylacrylic acid methyl, 3,3-dimethylacrylic acid ethyl, 2-methyl- 2-pentanoic acid methyl, 2-methyl-2-pentanoic acid ethyl, 2-ethyl-2-hexanoic acid methyl, 2-ethyl-2-hexanoic acid ethyl, 2-octanoic acid methyl and 2-octanoic acid ethyl, and the like.

The reaction (1) and (2) in the Scheme I require catalyst, and as such mineral acid such as sulfuric acid, hydrochloric acid and nitric acid can be used, and especially sulfuric acid is preferred. In addition, organic acid such as benzenesulfonic acid, p-toluenesulfonic acid, methanesulfonic acid, ethanesulfonic acid and trifluoro acetic acid can be used, and p-toluensulfonic acid is preferred.

The moreover, tangstic acid, molybdic acid, and their heteropolyacid can be named as catalyst. Typical examples of heteropolyacid are $H_3PW_{12}O_{40}$, $H_4SiW_{12}O_{40}$, $H_4TiW_{12}O_{40}$, $H_5CoW_{12}O_{40}$, $H_5FeW_{12}O_{40}$, $H_6P_2W_{18}O_{62}$, $H_7PW_{11}O_{33}$, $H_4TiMo_{12}O_{40}$, $H_3PMo_{12}O_{40}$, $H_7PMo_{11}O_{39}$, $H_6P_2Mo_{18}O_{62}$, $H_4PMoW_{11}O_{40}$, $H_4PVMo_{11}O_{40}$, $H_4SiMo_{12}O_{40}$, $H_5PV_2Mo_{10}O_{40}$, $H_3PMo6W_6O_{40}$, $H_{0.5}Cs_{2.5}PW_{12}O_{40}$ and their corresponding hydrates. In addition, catalyst with carbon or silica as a carrier can benamed. $H_3PW_{12}O_{40}$, $H_3PMo_{12}O_{40}$ and their hydrates among these heteropolyacid are the most preferred.

Furthermore, cation exchange resin such as Amberlite IR120 (trade name) and H-type zeolite such as H-ZSM-5 can also be used.

Especially, fatty acid salts of the compound from the second group of periodic table represented by $3ZnO \cdot 2B_2O_3$, cadmium acetate, zinc acetate and calcium acetate in addition to mineral acids, heteropolyacids, organic acids, cation exchange resin and H-type zeolite described above can be used as examples of catalyst for transesterification method.

The amount of these catalyst used can be 0.1–100% by weight based on DOL or DH-DOL, and economically speaking 1–20% by weight is preferable.

Over excess amount of acrylic acid compound or acrylic acid ester compound can be used in the reactions (1) and (2) in Scheme I, but the use of solvent is normally more preferred as the reaction can be carried out in solvent after decreasing the amount of allylalcohol used to near theoretical value. The kinds of solvent used are for example halogenated hydrocarbon such as 1,2-dichloroethane (EDC) or 1,1,1-trichloroethane, aromatic hydrocarbon such as benzene, toluene or xylene, and ether such as 1,2-dimethoxyethaneether or diethyleneglycoldimethylether.

The amount of solvent used is 1–20 fold by weight, more preferably 1–6 fold by weight based on DOL or DH-DOL. The reaction temperature can be 50–200° C., more preferably 70–150° C. The reaction can be carried out under the normal pressure or increased pressure. The reaction time may be 1–50 hours, but it is practical to carry out the reaction in 2–12 hours under the normal circumstance.

The method of preparation for the reaction (3) in Scheme I will be described in the followings.

(Meth)acryl acid halide shown in the general formula [11] can be obtained by converting said (meth)acryl acid compound to acid halide with halogenated thionyl. Halogen atoms shown as radical X can be F, Cl, Br and I, but the cheapest Cl is normally selected. Typical example of said compounds are such as acryloylchloride, methacryloylchloride, tiglyloylchloride, 3,3-dimethylacryloylchloride, 2-methyl-2-pentenoylchloride, 2-ethyl-2-hexanoylchloride and 2-octyloylchloride. The amount used is preferably 2.0–2.5 equivalent to DOL or DH-DOL.

Bases such as branched alkylamine compound such as trimethylamine, triethylamine and tripropylamine, aromatic amine compound such as pyridine, aniline and N-methylaniline, cyclic alkylamine compound such as 1,5-diazabicyclo[4,3,0]-5-nonane (DBN), 1,4-diazabicyclo[2,2,2]octane (DBO) and 1,8-diazabicyclo[5,4,0]undece-7-ene (DBU), and metal carbonate such as sodium carbonate, sodium hydrogen carbonate and potassium carbonate are indispensable in the method shown in the reaction formula (3) in Scheme I. The preferred base among them is triethylamine or tripropylamine. The amount used is preferably 2.0–2.5 equivalent (same equivalent as acid chloride) to DOL or DH-DOL.

The preferred method for the reaction (3) in Scheme I is to use solvent. Typical example of solvent preferred are ether compound such as tetrahydrofuran (THF), 1,2dimethoxyethane, dioxane and 2-methoxyethylether, N,N-dimethylformamide (DMF), N,N-dimethylacetoamide (DMAc), N-methylpyrrolidone and 1,3-dimethyl-2-imidazolidinone (DMI). Among them, cheaper 1,2dimethoxyethane or DMF are preferred. The preferred amount to be used is 1–10 fold by weight, and especially 2–5 fold by weight based on DOL or DH-DOL.

The reaction temperature is preferably 0–100° C., and the most preferably 0–50° C. Water is added to hydrolyze acid chloride left after the reaction, solvent is distilled off, extracted with water insoluble solvent (ether system or ester system), and then purified by distillation or column chromatography to obtain the desired compound.

In addition, tricyclo[5.2.1.0$^{2,6}$]decane compound or tricyclo[5.2.1.0$^{2,6}$]dece-3-ene compound where both A$^1$ and A$^2$ are 2-vinyloxyethyl group or either A$^1$ or A$^2$ is 2-vinyloxyethyl while the other is hydrogen can be synthesized by the Reaction Scheme II described below.

(2) 8-hydroxymethyl-9-(2-vinyloxyethyl)oxymethyl-tricyclo[5.2.1.0$^{2,6}$]decane (DH-DOLMV) can be obtained by reacting 8,9-bis(hydroxymethyl)tricyclo[5.2.1.0$^{2,6}$] decane (DH-DOL) and HVE under the existence of bases.

(3) 8,9-bis[(2-vinyloxyethyl)oxymethyl]tricyclo[5.2.1.0$^{2,6}$]dece-3-ene (DOLVE) can be obtained by reacting DOL and 2 mole fold of HVE under the existence of bases.

(4) 8,9-bis[(2-vinyloxyethyl)oxymethyl]tricyclo[5.2.1.0$^{2,6}$]decane (DH-DOLVE) can be obtained by reacting DH-DOL and 2 mole fold of HVE under the existence of bases.

Reaction Scheme II

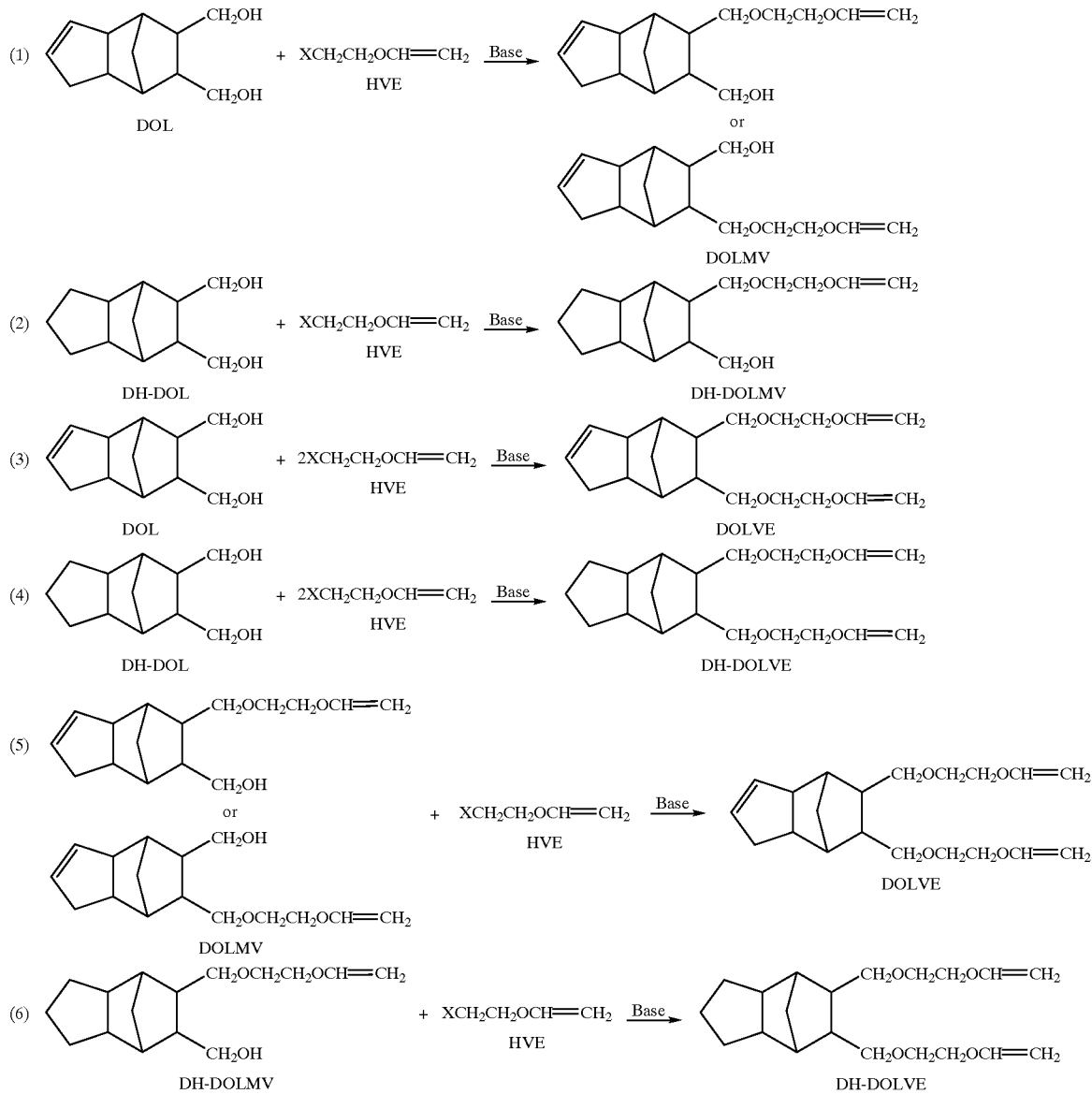

wherein X is halogen atom.

Namely, (1) 8(or 9)-hydroxymethyl-9(or 8)-(2-vinyloxyethyl)oxymethyl-tricyclo[5.2.1.0$^{2,6}$]dece-3-ene (DOLMV) can be obtained by reacting 8,9-bis (hydroxymethyl)tricyclo[5.2.1.0$^{2,6}$]dece-3-ene (DOL) and 2-haloethylvinylether (HVE) under the existence of bases.

(5) DOLVE can be obtained by reacting DOLMV and HVE under the existence of bases. (6) DH-DOLVE can be obtained by reacting DH-DOLMV and HVE under the existence of bases.

On this occasion, typical examples of 2-haloethylvinylether, an other raw material in addition to DOL and DH-DOL, shown in the formula [12] below

XCH$_2$CH$_2$OCH=CH$_2$  [12]

wherein X is halogen atom, are 2-fluoroethylvinylether, 2-chloroethylvinylether, 2-bromoethylvinylether and 2-iodoethylvinylether, and 2-chloroethylvinylether is used from the economical stand point of view. The preferred amount to be used is 1–10 mole fold, especially 2–5 mole fold, based on DOL or DH-DOL.

The existence of bases is indispensable for the reaction (1)–(6) in Scheme II above. The kind of bases that can be used may be hydroxide or hydride of alkaline metal and alkaline earth metal. Concrete examples are such as LiOH, NaOH, KOH, RbOH, CsOH, Mg (OH)$_2$, Ca (OH)$_2$, Sr (OH)$_2$, Ba (OH)$_2$, LiH, NaH, KH, MgH$_2$, CaH$_2$, SrH$_2$ and Ba (OH)$_2$. Especially, NaOH, KOH, Ca (OH)$_2$, Ba (OH)$_2$, NaH and KH are preferred. The amount to be used is 1–10 mole fold, and especially 2–5 mole fold is preferred based on the reaction substrate.

The use of organic solvent is also preferred for the reaction (1)–(6) in Scheme II. The kind of organic solvent preferred are amide family solvent such as N,N-dimethylformamide (DMF), N,N-dimethylacetoamide (DMAc) or N-methylpyrrolidone, sulfoxide family solvent such as dimethylsulfoxide (DMSO) or sulfolane, aliphatic hydrocarbon family solvent such as hexane, heptane or cyclohexane, aromatic hydrocarbon family solvent such as toluene, xylene or ethylbenzene, ether family solvent such as dioxane, tetrahydrofuran (THF), 1,2-dimethoxyethane (DME) or diethylglycoldimethylether and water, one or more than two kinds can be used in homogeneous system or two phase system. The amount to be used may be 1–20 fold by weight, and especially 2–5 fold by weight is economical based on the reaction substrate.

Furthermore, the use of phase transfer catalyst is also effective for the reaction (1)–(6) in Scheme II. The use of phase transfer catalyst is productive, for example when alkaline metal or alkaline earth metal is to be used in amide family solvent or when alkaline metal or alkaline earth metal is to be used in the two phase solvent system with hydrocarbon solvent and water. Examples of phase transfer catalyst are such as tetrabutylammonium chloride, tetrabutylammonium bromide, trimethylbenzylammonium chloride, triethylbenzylammonium chloride, tetramethylammnoium chloride, tetraethylammonium bromide, tetra-n-butylammonium hydrogensulfate, trimethylbenzylammonium hydroxide methanol solution and tetra-n-butylammonium hydroxide solution.

The amount to be used is 0.1–20% by weight, and preferably 0.5–10% by weight based on the reaction substrate is appropriate.

The reaction temperature is usually 0–150° C., but the reaction temperature of 40–120° C. is preferred so as to increase the yield of the desired compound. The reaction can be carried out under the normal pressure or increased pressure.

The reaction time varies depending upon the kind of bases, amount, reaction temperature and solvent among other factors, but it is normally carried out in 1–50 hours and the condition in which it can be over in 2–20 hours is preferred. The reaction can be carried out by the batch method or the continuous method.

The reaction can be followed by sampling the reaction solution and analyzing on gas chromatography. The isolation of the product can be done by adding water and isopropylether, ethyl acetate or methylethylketone (MEK) among others, dehydrating and concentrating the organic phase, and the residue can be purified by distilling and/or applying column chromatography to obtain the final product.

Acryloyl group or methacryloyl group thus obtained in the present invention, or alicyclic compound having 2-vinyloxyethyl group can be used as a monomer component of curable resin. In this instance, the monomer of the present invention alone can be used, but the use in combination with other acrylic family monomer is generally the norm. As things are, polymerization is carried out with catalyst (polymerization initiator) and solvent if necessary.

The monomer which can be used in combination are, without limitation, for example trimethylpropanetriacrylate, 1,6-hexanedioldiacrylate, neopentylglycoldiacrylate, trimethylolpropanedipropoxytriacrylate, polyethyleneglycoldiacrylate, tetrahydrofurfurylacrylate, 4•5,8bis(acryloyloxymethyl)tricyclodecane, oxyethylenic bisphenol A diacrylate, (meth)acrylic acid of bisphenol A-type glycidylether, (meth)acrylate of phenol novolac-type polyepoxy compound, methyl(meth)acrylate, carboxytricyclodecanylmethyl(meth)acrylate, 2-methyladamantyl(meth)acrylate, trimethylnorbornyl (meth)acrylate, hydroxymenthyl(meth)acrylate and hydroxypivalic acid neopentylglycol.

The amount to be used of monomer such as (meth) acrylate other than those described above is less than 80% by weight, and preferably less than 70% by weight based on the total amount of the composition including the compound of the present invention. The performance such as the adhesion of curable product can not be met if the amount to be used exceeds over 80% by weight.

The initiator is normally added into the compound of the present invention or the curable resin composition containing said compound in order to accelerate the cure reaction. For example, radical polymerization initiator is used for cure reaction with heat energy. Typical examples of the radical polymerization initiator are without limitation organic peroxide such as benzoylperoxide, acetylperoxide, di-t-butylperoxide, t-butylperoxylaurate, dicumylperoxide, α,α'-bis-t-butylperoxy-p-diisopropylbenzene, 2,5-dimethyl-2,5-di-t-butylperoxyhexane, 2,5-di-t-butylperoxyhexene, t-butyl peroxybenzoate, n-butyl-4,4-bis-t-butylperoxyvalerate, p-menthanehydroperoxide and t-butylcumylperoxide, or azobis compound such as 2,2'-azobis(isobutyinitril), 2,2'-azobis(2,4,4-trimethylvaleronitril) and 2,2'-azobis(2-cyclopropylpropionitril).

Light polymerization initiator is used for cure reaction with energy rays. Known light polymerization initiator can be used for this purpose and examples as such are, without limitation, benzoin, benzoinmethylether, benzoinethylether, benzoinisopropylether, benzoinbutylether, benzoinphenylether, 1-hydroxycyclohexylphenylketone, 3-methylacetophenone, 2,2-dimethoxyacetophenone, 2,2-dimethoxy-2-phenylacetophenone, 4-dialkylaminoacetophenone, 2-phenylthioacetophenone, benzyl, benzyldimethylketal, benzoylbezoate, anthraquinone, 2-ethylanthraquinone, naphthoquinone, 2,4-diisopropylthioxanthone, azobisisobutyronitril, 2,2'-azobis-2,4-dimethylvaleronitril, benzoylperoxide, di-t-butylperoxide, diphenyldisulfide, tetramethylthiurammonosulfide, tetraethylthiuramdisulfide, benzophenone, pivaloinethylether, dibenzylsulfide, cinnamoylchloride, dimethyldiphenylenedisulfide and dibenzothiazoledisulfide.

Furthermore, triboronfluoride ether, titanic acid tetraisopropyl and the like may also be used as a cation polymerization initiator.

The amount of these radical polymerization initiator, light polymerization initiator and cation polymerization initiator to be used is more than 0.01% by weight but less than 5% by weight, and preferably more than 0.05% by weight but less than 3% by weight based on the compound of the present invention or the curable resin composition having said compound thereof. The cure rate is not practical if it is less than 0.01% by weight. In addition, if it exceeds 5% by weight, then anymore improvement effect for cure rate can be expected and the weight, then anymore improvement effect for cure rate can be expected and the performance of the cured film decreases, so it is not preferred.

The sensitizer can be added so as to potentiate the effect of light polymerization initiator into the compound of the present invention which initiates the cure reaction with energy rays or the curable resin composition having said compound therein. The sensitizer can not by itself be activated with the irradiation of energy rays, but the combination increases the effectiveness when used together with light initiator than light initiator alone. Typical examples are, without limitation, such as triethylamine, triethyltetramine, n-butylamine, di-n-butylamine, tri-n-butylphosphine, allylthiourea, s-benzylisothiuranium-p-toluenesulfinate and diethylaminoethylmethacrylate.

The amount of the sensitizer to be used is more than 0.01% by weight but less than 5% by weight, and preferably more than 0.05% by weight but less than 3% by weight based on the compound of the present invention or the curable resin composition having said compound therein. If it is less than 0.01% by weight, cure rate is too slow to be practical. In addition, if it exceeds 5% by weight, then anymore improvement effect as the sensitizer can be expected and the performance of the cured film decreases, so it is not preferred.

Examples of the solvent used for polymerization are cyclic ether group such as tetrahydrofuran and dioxane, glycol ether group such as ethyleneglycolmonomethylether, ethyleneglycolmonoethylether, diethyleneglycolmonomethylether, diethyleneglycolmonoethylether and diethyleneglycoldimethylether, propyleneglycolalkylether acetate group such as propyleneglycol (mono) methylether acetate and propyleneglycolpropylether acetate, ketone group such as methylethylketone, cyclohexanone and 4-hydroxy4-methyl-2-pentanone, ester group such as 2-hydroxypropinic acid ethyl, 2-hydroxy-2-methylpropionic acid ethyl, 2-hydroxy-2-methylpropionic acid ethyl, ethoxyethyl acetate, hydroxy acid ethyl, 2-hydroxy-3-methylbutanoic acid methyl, 3-methoxypropionic acid methyl, 3-methoxypropionic acid ethyl, 3-ethoxypropionic acid ethyl, 3-ethoxypropionic acid methyl, ethyl acetate, butyl acetate, methyl lactate and ethyl lactate, cellosolve ester group such as methyl cellosolve acetate and ethyl cellosolve acetate, aromatic hydrocarbon group such as benzene, toluen and xylene, and aprotic polar solvent such as DMF under the normal circumstances 20–1000 parts by weight to the total 100 parts by weight of polymeric component.

In the present invention, components such as inorganic filler materials, leveling agents, colorant, for example, pigment or dye, anti-forming agent, adhesive property impartant, plasticizer, solvent and storage stabilizer can be added at need to the compound of the present invention or the curable resin composition having said compound therein.

As for the compound of the present invention in which energy rays leads to cure reaction or the curable resin composition having said compound therein, typical examples of active light in order for the cure reaction to be taken place with the irradiation over the compound or the composition are ultraviolet rays, electron rays or X-rays.

Sun light, chemical lamp, low pressure mercury vapor lamp, high pressure mercury vapor lamp, metal halide lamp or xenon lamp among others can be used as the light source for ultraviolet rays.

The field of application for the curable resin composition having said alicyclic compound of the present invention are such as adhesive, paint, ink, building material, lighting, glass fiber reinforced resin, rust and corrosion prevention, optical lens, optical fiber coating, UV•EB curable resin and resist.

Especially, the alicyclic compound of the present invention excels as photosensitive monomer suitable for resist raw material because of high clarity at short wavelength ultraviolet rays, high dry etching resistance due to tricyclic ring structure and strong adhesive property against silicone substrate, as the optic raw material and the disk overcoat raw material because of high clarity, low birefringence and low water absorption rate, and as the suitable coating raw material such as UV•EB curable coating material because of high reactivity, high wear characteristics and water resistance.

Furthermore, the compound of the present invention can also be used as the dental restoration raw material. They excel in for example adhesive property against dentin and blocking property for the vicinity of dentin and restoration material. In addition, the dental adhesive having mono (meth)acrylate compound with hydroxy group within the molecule of the present acrylate compound with hydroxy group within the molecule of the present invention have good balance for adhesive property, blocking property and hydrophilic nature among others.

BEST MODE FOR CARRYING OUT THE INVENTION

The present invention is described further in more details by showing the examples, but the invention is not limited to the particular embodiments described herein.

EXAMPLE 1

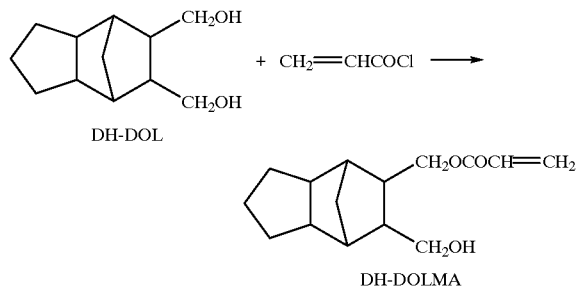

3.92 g (20 mmol) of DH-DOL, 40 ml of tetrahydrofuran (THF) and 2.02 g (20 mmol) of triethylamine were charged into a 100 ml 4-mouthed reaction flask and cooled to 5° C. Under stirring, the mixed solution of 1.82 g (20 mmol) of acryloylchloride and 10 ml of THF was added drop-wise. The reaction solution was stirred for one hour at 5° C. and then further reacted for 6 hours at 25° C. The reaction solution was filtered and the filtrate was concentrated. The residue was dissolved in chloroform, washed with 0.5 N-hydrochloric acid solution, saturated salt solution, 3% sodium carbonate solution and saturated salt solution in succession, and concentrated under the reduced pressure after dehydration with anhydrous magnesium sulfate. The concentrated residue was purified through the silica gel column chromatography with n-hexane/ethyl acetate=4/1 to yield 1.14 g (Yield 23%) of 8-acryloyloxymethyl-9-hydroxymethyltricyclo[5.2.1.0$^{2,6}$]decane (DH-DOLMA) and 1.25 g (Yield 21%) of 8,9-bis(acryloyloxymethyl)tricyclo[5.2.1.0$^{2,6}$]decane (DH-DOLDA) were obtained.

The structure of DH-DOLMA was confirmed with the analytical results described below.

MASS (FAB$^+$, m/e (%)): 251 (M$^+$1, 16), 220 (25), 179 (27), 177 (47), 161 (92), 133 (35), 119 (44), 101 (67), 94 (100), 84 (63), 71 (40). $^1$H-NMR (CDCl$_3$, δ ppm): 1.37 (dt, $J_1$=10.25 Hz, $J_2$=1.47 Hz, 1H), 1.48–1.69 (m, 7H), 2.06 (d, J=12.0 Hz, 2H), 2.12 (d, J=7.7 Hz, 1H), 2.15 (s, 1H), 2.24 (dd, $J_1$=15.29 Hz, $J_2$=8.33 Hz, 1H), 2.44 (d, J=2.56 Hz, 2H), 3.49 (dd, $J_1$=10.62 Hz, $J_2$=7.69 Hz, 1H), 3.69 (dd, $J_1$=10.53 Hz, $J_2$=6.68 Hz, 1H), 4.06 (dd, $J_1$=11.08 Hz, $J_2$=8.33 Hz, 1H), 4.25 (dd, $J_1$=10.99 Hz, $J_2$=6.59 Hz, 1H), 5.83 (dd, $J_1$=8.61 Hz, $J_2$=1.47 Hz, 1H), 6.12 (dd, $J_1$=17.30 Hz, $J_2$=10.34 Hz, 1H), 6.40 (dd, $J_1$=17.39 Hz, $J_2$=1.47 Hz, 1H). $^{13}$C-NMR (CDCl$_3$, δ ppm): 26.78 (2), 29.01, 37.11, 38.31, 40.71 (2), 44.68, 45.02, 45.53, 45.59, 62.92, 65.16, 128.50, 130.8, 166.29. IR (KBr, cm$^{-1}$): 3420, 2950, 1720, 1410, 1300, 1200, 1050, 1020, 980, 810.

EXAMPLE 2

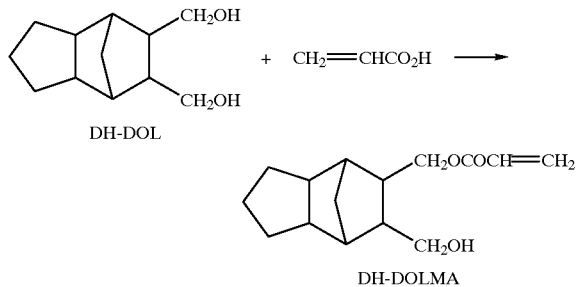

DH-DOL

DH-DOLMA 7.84 g (40 mmol) of DH-DOL, 3.24 g (45 mmol) of acrylic acid, 0.23 g of p-toluene sulfonic acid monohydrate, 0.20 g of hydroquinone and 20 ml of benzene were charged into a 100 ml 4-mouthed reaction flask, the mixture was stirred for 4 hours while the product water was distilled off with the concomitant increase in the temperature from 90–104° C. The mixture was cooled after the completion of the reaction and then 1,2-dichloroethane (EDC) and water were added, and EDC layer was washed with saturated salt solution, 5% sodium hydrogen carbonate solution and again saturated salt solution in succession. This EDC layer was concentrated under reduced pressure and the residue was purified through the silica gel column chromatography to yield 2.08 g (Yield 21%) of DH-DOLMA of the object.

EXAMPLE 3

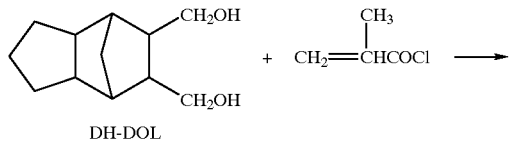

DH-DOL

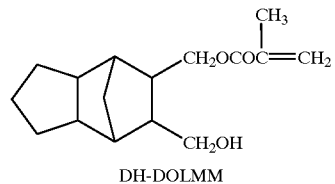

DH-DOLMM 3.92 g (20 mmol) of DH-DOL, 30 g of THF and 2.02 g (20 mmol) of triethylamine were charged into a 100 ml 4-mouthed reaction flask and cooled to 5° C. The mixed solution of 2.09 g (20 mmol) of methacryloylchloride and 10 g of THF was drop-wise added into the reaction mixture with stirring. Stirring was continued for one hour at 5° C. and then the mixture was additionally reacted for 6 hours at 25° C. The mixture was concentrated under reduced pressure at 25° C. and then 1,2-dichloroethane (EDC) and water were added to the residue and EDC layer was separated. This EDC layer was washed with 0.5%-hydrochloric acid solution, saturated salt solution, 3% sodium hydrogen carbonate solution, and again saturated salt solution in succession, and the layer was dried with anhydrous sodium sulfate and concentrated under reduced pressure. This concentrated residue was purified through the silica gel column chromatography with n-hexane/ethyl acetate=4/1 to yield 1.48 g (Yield 28%) of 8-methacryloyloxymethyl-9-hydroxymethyltricyclo[5.2.1.0$^{2,6}$]decane (DH-DOLMM) and 1.39 g (Yeld 21%) of 8,9-bis(methacryloyloxymethyl)tricyclo[5.2.1.0$^{2,6}$]decane (DH-DOLDM).

The structure of DH-DOLMM was confirmed with the analytical results described below.

MASS (FD$^+$, m/e (%)):265 (M$^+$1, 55), 178 (100). $^1$H-NMR (CDCl$_3$, δ ppm): 1.27 (s, 2H), 1.48–1.68 (m, 9H), 1.95 (s, 3H), 2.07 (d, J=15.5 Hz, 2H), 2.45 (s, 2H), 3.48 (dd, $J_1$=8.05 Hz, $J_2$=10.25 Hz, 1H), 3.68 (dd, $J_1$=6.77 Hz, $J_2$=10.44 Hz, 1H), 4.04 (dd, $J_1$=8.51 Hz, $J_2$=10.89 Hz, 1H), 4.24 (dd, $J_1$=6.23 Hz, $J_2$=10.99 Hz, 1H), 5.56 (dd, $J_1$=1.47 Hz, $J_2$=3.11 Hz, 1H), 6.09 (s, 1H), $^{13}$C=NMR (CDCl$_3$, δ ppm): 14.13, 18.30, 22.71, 26.82, 29.04, 31.90, 37.13, 38.26, 40.67, 44.69, 45.62, 62.7, 65.24, 125.45, 136.38, 167.50.

EXAMPLE 4

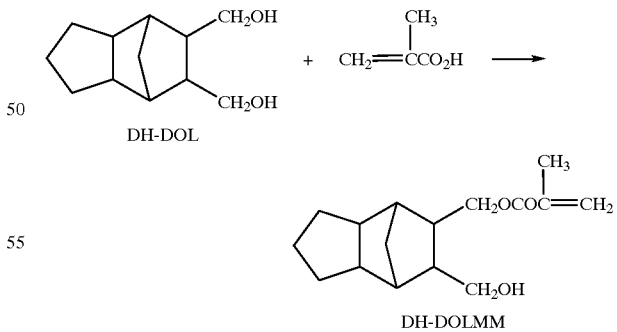

DH-DOL

DH-DOLMM 7.84 g (40 mmol) of DH-DOL, 3.87 g (45 mmol) of methacrylic acid, 0.23 g of p-toluene sulfonic acid monohydrate, 0.20 g of hydroxyquinone and 20 ml of benzene were charged into a 100 ml 4-mouthed reaction flask, and the mixture was stirred for 4 hours while the product water was distilled off with the concomitant increase in the temperature from 90–106° C. The mixture was cooled after the completion of the reaction and then 1,2-dichloroethane (EDC) and water were added, and EDC layer was washed with saturated salt solution, 5% sodium hydrogen carbonate solution and again saturated salt solution in succession. After this EDC layer was concentrated under reduced pressure, the residue was purified through the silica gel column chromatography to yield 1.19 g (Yield 18%) of DH-DOLMM of the object.

EXAMPLE 5

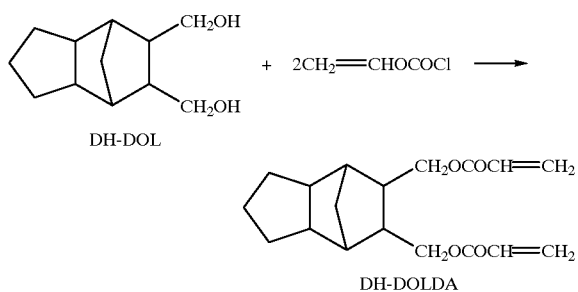

422 g (2.15 mole) of DH-DOL was dissolved into 6 L of tetrahydrofuran (THF), and 438 g (4.84 mole) of acryloylchloride was added. 480 g (4.84 mole) of triethylamine was drop-wise added into the mixture over 30 minutes after cooled to 0° C. After the completion of drop-wise addition, the reaction was completed two hours after gradually raising the temperature to room temperature (25° C.). The mixture was concentrated under reduced pressure after the addition of 3 L of water and THF was distilled off. The pH of water layer was adjusted to pH 8 with triethylamine and then extracted with diisopropylether thrice. The extracted solution were combined and concentrated under reduced pressure, and then the residue was purified through the silica gel column ($SiO_2$: 3 Kg×2, eluate: n-hexane/ethyl acetate= 10/1). 510 g (Yield 77.9%) of oily product was obtained at the room temperature as the main fraction. Incidentally, this oily product became solidified after kept in −40° C. refrigerator over night and then returned to the room temperature. The analytical results of this crystal were as follows.

Melting point (° C): 33–34; MASS (FD$^+$, m/e (%)): 304 (M$^+$, 100), 160 (45). $^1$H=NMR (CDCl$_3$, δ ppm): 1.41 (d, J=10.3 Hz, 2H), 2.08 (s, 2H), 2.26–2.29 (m, 2H), 2.46 (s, 2H), 4.06–4.10 (m, 2H), 4.20 (dd, J$_1$=5.86 Hz, J$_2$=11.0 Hz, 2H), 5.83 (dd, J$_1$=1.47 Hz, J$_2$=10.4 Hz, 2H), 6.13 (c, J$_1$=10.4 Hz, J$_2$=17.2 Hz, 2H), 6.41 (dd, J$_1$=1.47 Hz, J$_2$=1.72 Hz, 2H).

From the results described above, the product was confirmed as 8.9-bis(acryloyloxymethyl)tricyclo[5.2.1.0$^{2,6}$]decane.

EXAMPLE 6

7.84 g (40 mmol) of DH-DOL, 6.48 g (90 mmol) of acrylic acid, 0.23 g of p-toluene sulfonic acid, 0.20 g of hydroxyquinone and 4 ml of benzene were mixed and stirred with the removal of water while raising the temperature to 90–106° C. After the reaction was completed, the mixture was concentrated under the reduced pressure after the addition of 1.4 ml of water. The mixture was extracted with the addition of 20 ml of diisopropylether and then washed with 5% NaCl solution, 2% NaOH solution and further 5% NaCl solution. After the concentration under reduced pressure, the residue was purified through the silica gel to yield 3.5 g (Yield 28.7%) of 8,9-bis(acryloyloxymethyl)tricyclo [5.2.1.0$^{2,6}$]decane of the object.

EXAMPLE 7

340 g (1.73 mole) of DH-DOL was dissolved into 5.1 L of tetrahydrofuran (THF) and then 526 g (5.19 mole) of triethylamine was added. 408 g (5.19 mole) of methacryloyloxychloride was drop-wise added to this mixture after the mixture was cooled to 0° C. After the completion of drop-wise addition, the mixture was continuously stirred for three hours while gradually raising the temperature to room temperature (25° C.) to complete the reaction. Then, the mixture was concentrated under the reduced pressure after the addition of water, and THF was distilled off. Isopropylether (IPE) was added to the residue and the product was extracted.

This IPE solution was concentrated under the reduced pressure to yield 550 g of white crystal. This impure crystal was re-crystallized with n-hexane/ethyl acetate=20/1 to yield 110.3 g of white crystal with 99.1% purity with liquid chromatography. The filtrate was further purified through the silica gel column ($SiO_2$: 5 Kg) after concentration to yield 206.6 g of white crystal with 99.3% purity with liquid chromatography. The same product was obtained after re-crystallization. The results are described below.

Melting point (° C): 72–73; MASS (FD$^+$, m/e (%)): 332 (M$^+$, 100), 279 (35). $^1$H-NMR (CDCl$_3$, δ ppm): 1.41 (d, J=10.3 Hz, 1H), 1.41 (d, J=10.3 Hz, 1H), 1.52–1.56 (m, 6H), 1.70 (d, J=10.3 Hz, 1H), 1.95 (s, 6H), 2.09 (s, 2H), 2.27 (t, J=3.9 Hz, 2H), 2.46 (s, 2H), 4.04–4.09 (m, 2H), 4.19–4.22 (m, 2H), 5.56 (s, 2H), 6.11 (s, 2H).

From the results described above, the product was confirmed as 8,9-bis(methacryloyloxymnethyl)tricyclo [5.2.1.0$^{2,6}$]decane.

EXAMPLE 8

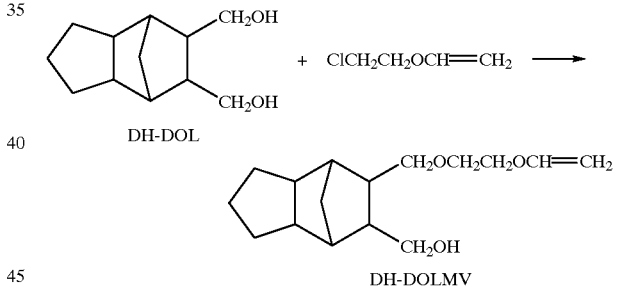

20 g (102 mmol) of 8,9-bis(hydroxymethyl)tricyclo [5.2.1.0$^{2,6}$]decane (DH-DOL), 13.47 g (204 mmol) of 85% potassium hydroxide and 90 ml of DMSO were charged into a 300 ml 4-mouthed reaction flask and heated to 60° C. Next, 43.47 g (408 mmol) of 2chloroethylvinylether (VEC) was drop-wise added at 70° C. The mixture was then stirred for three hours at 75–80° C. 6.74 g (102 mmol) of 85% potassium hydroxide and 21.74 g (204 mmol) of VEC were further added. The mixture was stirred for another one hour with heating and the reaction mixture was tested on the thin chromatography, and only the product was identified concomitant with the disappearance of raw materials.

Next, water and ethyl acetate were added to the reaction mixture, and the organic layer was washed with water, dehydrated with anhydrous magnesium sulfate and concentrated under the reduced pressure. The concentrated residue was purified through the silica gel column chromatography with n-hexane/ethyl acetate=6/1–2/1 to yield 27.8 g (Yield 100%) of oily product (later solidified upon storage at 5° C.). The analytical results of this product were as follows.

Melting point (° C): 33–34; MASS (FD$^+$, m/e (%)): 266 (M$^+$, 100), 249 (18), 194 (13). $^1$H-NMR (CDCl$_3$, δ ppm): 1.32 (d, J=8.4 Hz, 1H), 1.49 (d, J=9.8 Hz, 3H), 1.55–1.64 (m, 4H), 1.88 (d, J=12.4 Hz, 2H), 2.17 (s, 1H), 2.31 (s, 1H), 2.39 (s, 2H), 3.40–3.45 (m, 2H), 3.64–3.75 (m, 5H), 3.83 (t, J=4.0 Hz, 2H), 4.01–4.04 (m, 1H), 4.16–4.20 (m, 1H), 6.47–6.52 (m, 1H). $^{13}$C-NMR (CDCl$_3$, δ ppm): 26.71, 26.76, 29.00, 38.09, 39.68, 41.66, 45.62, 45.72, 45.85, 45.94, 64.04, 66.79, 69.30, 73.52, 86.85, 151.56.

From the results described above, the product was confirmed as 8-hydroxymethyl-9-(2-vinyloxyethyl)oxymethyl-tricyclo[5.2.1.0$^{2,6}$]decane.

EXAMPLE 9

1.96 g (10 mmol) of DH-DOL and 20 ml of DMF were charged into a 50 ml 4-mouthed reaction flask and 1 g (25 mmol) of 60% NaH was added with stirring in an ice bath. The temperature of the mixture was then gradually raised to room temperature to 50° C. and stirred for two hours. 2.67 g (25 mmol) of VEC was drop-wise added after the mixture was again cooled to 0° C. The temperature was adjusted to room temperature again and the then reaction was carried out for three hours. Water and ethyl acetate were added to the reaction mixture, and then the organic layer was washed with water and concentrated, and the concentrated residue was purified through the silica gel column chromatography to isolate 1.14 g (Yield 42.9%) of DH-DOLMV and 0.71 g (Recovery 36.2%) of DH-DOL, the raw material.

EXAMPLE 10

3.92 g (20 mmol) of DH-DOL and 60 ml of DMF were charged into a 100 ml 4-mouthed reaction flask and 4.8 g (120 mmol) of 60% NaH was added with stirring in an ice bath over 30 minutes. The temperature was gradually raised to room temperature to 100° C. and stirred for 18 hours. 8.53 g (80 mmol) of VEC was drop-wise added after the mixture was cooled again to 0° C. The temperature of the mixture was adjusted to room temperature again and the reaction was carried out for three hours. Water and ethyl acetate were added, and the organic layer was washed with water and concentrated, and the concentrated residue was purified through the silica gel column chromatography to isolate 3.68 g (Yield 69.1%) of DH-DOLMV and 0.82 g (Recovery 21.0%) of DH-DOLO, the raw material.

EXAMPLE 11

1.96 g (10 mmol) of DH-DOL, 10 ml of toluene, 3.96 g (60 mmol) of 85% KOH, 10 ml of water and 1.29 g (4 mmol) of tetrabutylammonium bromide were charged into a 50 ml 4-mouthed reaction flask and 4.26 g (40mmol) of VEC was drop-wise added with stirring. After the temperature was raised to 70° C. and the reaction was carried out for 67 hours, 2.13 g (20 mmol) of VEC was further added and reacted for 24 hours. After the mixture was cooled and separated with the addition of water, the water layer was extracted with ethyl acetate, the combined organic layer was washed with water, then dehydrated with anhydrous magnesium sulfate and concentrated under the reduced pressure. The concentrated residue was purified through the silica gel column chromatography with n-hexane/ethyl acetate=6/1–2/1 to yield 1.85 g (Yield 70%) of DH-DOLMV and 1.07 g (Yield 28%) of a new component. The analytical results for this new oily product are as described below.

MASS (FD$^+$, m/e (%)): 336 (M$^+$, 100), 269 (28), 249 (19), 195 (23). $^1$H-NMR (CDCl$_3$, δ ppm): 1.30 (d, J=9.9 Hz, 1H), 1.48 (d, J=9.0 Hz, 1H), 1.59 (dd, J$_1$=12.8 Hz, J$_2$=10.3 Hz, 6H), 2.05 (s, 2H), 2.16 (d, J=11.5 Hz, 2H), 2.40 (s, 2H), 3.33 (dd, J$_1$=1.5 Hz, J$_2$=7.6 Hz, 2H), 3.51–3.54 (m, 2H), 3.59–3.66 (m, 4H), 3.79–3.83 (m, 4H), 3.99–4.01 (m, 2H), 4.18 (dd, J$_1$=12.2 Hz, J$_2$=2.1 Hz, 2H), 6.50 (dd, J$_1$=7.47 Hz, J$_2$=5.87 Hz, 2H). $^{13}$C-NMR (CDCl$_3$, δ ppm): 26.78, 29.06, 37.83, 38.56, 44.98, 45.73, 67.44, 69.13, 71.96, 76.82, 86.61, 151.89.

From the results obtained above, the product was confirmed as 8,9-bis[(2-vinyloxyethyl)oxymethyl]tricyclo [5.2.1.0$^{2,6}$]decane (DH-DOLVE).

EXAMPLE 12

145 g (0.74 mmol) of DH-DOL, 40 ml of toluene, 95.4 g (0.3 mmol) of tetrabutyl ammonium bromide, 293 g (4.44 mmol) of 85% KOH and 740 ml of water were charged into a 2 L 4-mouthed reaction flask and 315.5 g (2.96 mmol) of VEC was drop-wise added with stirring at room temperature. The temperature was raised to 70° C. and continuously stirred for 95 hours. After the further addition of 139.5 g (1.31 mmol) of VEC, the reaction was carried out for 28 hours. Water was added after cooling, toluene layer was separated, the water layer was extracted with ethyl acetate and mixed with toluene layer, and then dehydrated with anhydrous magnesium sulfate to yield the oily product upon concentration. After the addition of 0.5 g of hydroquinone to this oily product and impurities with low boiling point were removed by distillation under the reduced pressure (oil bath 106–135° C./1.6 mm Hg), and the residue was purified through the silica gel column chromatography with n-hexane/ethyl acetate=6/1–2/1. The obtained impure DH-DOLVE and impure DH-DOLMV were each dissolved into acetone, decolored with activated charcoal (5% addition), filtered and then distilled off acetone to yield 41 g (Yield 16%) of DH-DOLVE and 123 g (Yield 63%) of DH-DOLMV (stabilizer: addtion of about 100 ppm of hydroquinone monomethylether).

EXAMPLE 13

1.96 g (10 mmol) of DH-DOL, 3.5 ml of DMSO and 1.32 g (20 mmol) of 85% KOH were charged into a 50 ml 4-mouthed reaction flask and stirred for one hour at 60° C. After the drop-wise addition of 4.26 g (40 mmol) of VEC at 70° C., the mixture was stirred for three hours at 75–80° C. 0.32 g (1 mmol) of tetrabutyl ammoniumbromide, 0.66 g (10 mmol) of 85% KOH and 2.13 g (20 mmol) of VEC were further added and the mixture was stirred for one hour with heating. Although DH-DOL, the raw material, disappeared, 0.66 g (10 mmol) of 85% KOH and 2.13 g (20 mmol) of VEC were further added and stirred for 5 hours with heating. Water and ethyl acetate were added after cooling, the organic layer was washed with water, dehydrated with anhydrous magnesium sulfate, and concentrated. The concentrated residue was purified through the silica gel column chromatography to yield 0.58 g (Yield 17%) DH-DOLVE and 1.89 g (Yield 71%) of DH-DOLMV.

EXAMPLE 14

2.66 g (10 mmol) of DH-DOLMV, 10 ml of toluene, 0.32 g (1 mmol) of tetrabutyl ammoniumbromide and 0.8 g (20 mmol) of NaOH dissolved in 5 ml water were charged into a 50 ml 4-mouthed reaction flask and the mixture was stirred for one hour at 60° C. Next, 4.26 g (40 mmol) of VEC was drop-wise added at 70° C. The temperature of the mixture was raised to 75–80° C. and stirred for three hours. After the further addition of 2.0 g (50 mmol) of NaOH, 4.26 g (40 mmol) of VEC was added and stirred for three hours. After the reaction was completed, toluene layer was separated and combined with the extract of water layer with ethyl acetate, dehydrated with anhydrous magnesium sulfate to yield the oily product upon concentration. The oily product was purified through the silica gel column chromatography to yield 1.25 g (Yield 37%) of DH-DOLVE with 95.8% purity with gas chromatography.

EXAMPLE 15

2.66 g (10 mmol) of DH-DOLMV obtained in Example 12, 10 ml of DMSO and 1.32 g (20 mmol) of 85% KOH were charged into a 50 ml 4-mouthed reaction flask and stirred for one hour at 60° C. After the further addition of 4.26 g (40 mmol) of VEC drop-wise at 70° C., the mixture was stirred for three hours at 75–80° C. After the addition of 1.32 g (20 mmol) of 85% KOH, additional 4.26 g (40 mmol) of VEC was added and stirred continuously for three hours. Water and ethyl acetate were added after the reaction solution was cooled to room temperature, and the organic layer was dehydrated with anhydrous magnesium sulfate, then concentrated, and the residue was purified through the silica gel column chromatography to yield 0.98 g (Yield 29%) of DH-DOLVE.

EXAMPLE 16
(DG-DOLDA photo-setting and characteristics)

A sample with following composition was prepared and used for the evaluation. 5 parts by weight of 1-hydroxycyclohexylphenylketone (produced by Ciba Speciality Chemicals Co., Irgcure-184®) as a light polymerization initiator was added to the composition comprising of 45 parts by weight of 8,9-bis(acryloyloxymethyl)tricyclo[5.2.1.0$^{2,6}$]decane (DH-DOLDA) obtained in Example 5, 20 parts by weight of trimethyrolpropanedipropoxytriacrylate (produced by Nihon Kayaku K.K., TPA-320®), 30 parts by weight of hydroxypivalic acid neopentylglycol (produced by Nihon Kaykaku K.K., KAYARAD-MANDA®) and 5 parts by weight of tetrahydrofurfurylacrylate (produced by Osak Yuki Co., THFA®). The obtained mixture was applied over the glass substrate by spincoating and then light-cured with a high-pressure mercury lamp until the complete loss of tack. Following characteristics were examined for the obtained coating.

1) Clarity; the transmission at 400 nm through the film with 3 $\mu$m in thickness on the quart substrate after curing was 98%. The haze was less than 0.1% and transparent.
2) Refractive index; 1.5097 (633 nm), birefringence 0.0000
3) Pencil hardness; HB
4) Water absorption rate; 0.62%
5) Heat resistance; 10% weight reduction temperature; 241° C.
6) Electrical characteristics; dielectric constant 3.25 (1 KHz), dielectric dissipation factor 0.0342 (1 KHz), volume resistance 5×10 15 $\Omega$cm
7) Adhesive property; cellophane tape peeling test was conducted after a cross cut was made on the bare silicon substrate, but peeling was not observed.

EXAMPLE 17
(Synthesis of DH-DOLMV homo-polymer)

Under nitrogen gas atmosphere, 2 g of 8-hydroxymethyl-9-(2-vinyloxyethyl)oxymethyl-tricyclo[5.2.1.0$^{2,6}$]decane (DH-DOLMV) was dissolved to 10% by weight in diglyme (diethyleneglycoldimethylether). Three drops of borontrifluorideether solution as a cation polymerization initiator was added with a pipette into this solution and cation polymerization was conducted at 70° C. for 24 hours with heating and constant stirring. The molecular weight distribution of the obtained polymer with gel filtration chromatography (polystyrene conversion) was confirmed and number-average molecular weight (Mn) was 8543, weight-average molecular weight (Mw) was 27337, and the ratio of Mw/Mn was 3.2.

EXAMPLE 18
(Synthesis of DH-DOLMA and acrylic acid methyl copolymer)

Under nitrogen gas atmosphere, 2.5 g of 8-acryloyloxymethyl-9-hydroxymethyltricyclo[5.2.1.0$^{2,6}$]decane (DH-DOLMA) and 2.5 g of acrylic acid methyl were dissolved in 20 g of cyclohexanone. 0.1 g of 2,2'-azobis (isobutylonitrile) was added into the solution as a polymerization initiator and radical polymerization was conducted at 70° C. for 24 hours with heating and constant stirring. The molecular weight distribution of the obtained polymer with gel filtration chromatography (polystyrene conversion) was confirmed and Mn was 7841, Mw was 29012, and the ratio of Mw/Mn was 3.7. Monomer to polymer conversion rate was followed with gas chromatography, but the conversion rate remains nearly the same and random copolymer was obtained.

EXAMPLE 19
(Synthesis of DH-DOLMA homo-polymer and their property)

Under nitrogen gas atmosphere, 2 g of 8-acryloyloxymethyl-9-hydroxymethyltricyclo[5.2.1.0$^{2,6}$]decan (DH-DOLMA) was dissolved into 20 g of the solution consisting of 2-heptanone and propyleneglycol monomethylether acetate with 1:1 weight ratio. 0.16 g of 2,2'-azobis (isobutylonitrile) was added into the solution as a radical polymerization initiator and radical polymerization was conducted at 70° C. for 24 hours with heating and constant stirring. The molecular weight distribution of the obtained polymer with gel filtration chromatography (polystyrene conversion) was confirmed and Mn was 2434, Mw was 5841, and the ratio of Mw/Mn was 2.4. Special properties as described below were investigated for the obtained polymer.

1) Refractive index; 1.536 (633 nm)
2) Water absorption rate; 0.61%
3) Heat resistance; 10% weight reduction temperature; 251° C.
4) Glass transition temperature; not detected up to 150° C. with differential scanning calorimetric measurement
5) Adhesive property; cellophane tape peeling test was conducted after a cross cut was made on the bare silicon substrate, but peeling was not observed.

INDUSTRIAL APPLICABILITY

Alicyclic compound of the present invention is industrially useful compound as a monomer for curable resin and the curable resin composition having said compound therein are suitable as resist raw materials because of dry etching resistance and the improvement in adhesive property, as optical raw materials and disk overcoat raw materials because of the improvement in clarity, low birefringence and low rate of water absorption and also as coating raw materials such as UV•EB cure coating because of reactivity, wear resistance and water resistance.

What is claimed is:

1. Tricyclo[5.2.1.0$^{2,6}$]decane compound or tricyclo[5.2.1.0$^{2,6}$]dece-3-ene compound shown in the formula [1] below

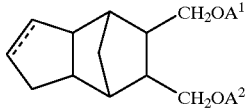

[1]

wherein A$^1$ and A$^2$ are independently hydrogen; or acryloyl or methacryloyl shown in the formula [2] below

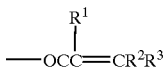

[2]

wherein R$^1$ is hydrogen or C$_1$–C$_4$ alkyl; and R$^2$ and R$^3$ are independently hydrogen or C$_1$–C$_{10}$ alkyl; or 2-vinyloxyethyl group shown in the formula [3] below

—CH$_2$CH$_2$OCH=CH$_2$ [3]

wherein the dofted line is single bond or double bond with the proviso that A$^1$ and A$^2$ are not hydrogen at the same time.

2. 8-(meth)acryloyloxymethyl-9-hydroxymethyltricyclo[5.2.1.0$^{2,6}$]decane compound or 9(or 8)-(meth)acryloyloxymethyl-8(or 9)-hydroxymethyltricyclo[5.2.1.0$^{2,6}$]dece-3-ene compound according to claim 1, where A$^1$ in the formula [1] is acryloyl group or methacryloylgroup as shown in the formula [2] below

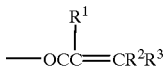

[2]

wherein R$^1$ is hydrogen or C$_1$–C$_4$ alkyl; R$^2$ and R$^3$ are independently hydrogen or C$_1$–C$_{10}$ alkyl; and A$^2$ is hydrogen as shown in the formula [4a] or [4b] below

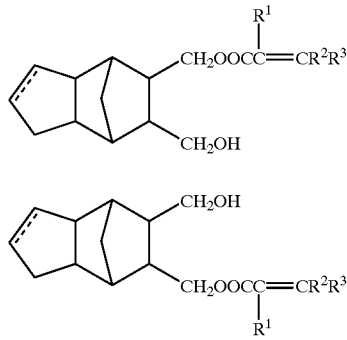

[4a]

[4b]

wherein R$^1$ is hydrogen or C$_1$–C$_4$ alkyl; R$^2$ and R$^3$ are independently hydrogen or C$_1$–C$_{10}$ alkyl; and the dotted line is single bond or double bond.

3. 8,9-bis((meth)acryloyloxymethyl)tricyclo[5.2.1.0$^{2,6}$]decane compound or 8,9-bis((meth)acryoyloxymethyl)tricyclo[5.2.1.0$^{2,6}$]dece-3-ene compound according to claim 1, where A$^1$ and A$^2$ are the same or different in the formula [1], and acryoyl group or methacryloyl group shown in the formula [2] below

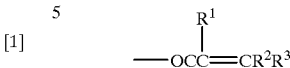

[2]

wherein R$^1$ is hydrogen or C$_1$–C$_4$ alkyl; R$^2$ and R$^3$ are independently hydrogen or C$_1$–C$_{10}$ alkyl; and shown in the formula [5] below

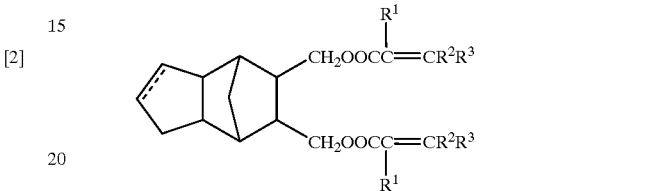

[5]

wherein R$^1$ is hydrogen or C$_1$–C$_4$ alkyl; R$^2$ and R$^3$ are independently hydrogen or C$_1$–C$_{10}$ alkyl; and the dotted line is single bond or double bond.

4. 8-hydroxymethyl-9-(2-vinyloxyethyl)oxymethyl-tricyclo[5.2.1.0$^{2,6}$]decane or 8(or 9)-hydroxymethyl-9(or 8)-(2-vinyloxyethyl)oxymethyl-tricyclo[5.2.1.0$^{2,6}$]dece-3-ene according to claim 1, where A$^1$ in the formula [1] is 2-vinyloxyethyl group shown in the formula [3] below

—CH$_2$CH$_2$OCH=CH$_2$ [3]

and A$^2$ is hydrogen, as shown in the formula [6a] or [6b] below

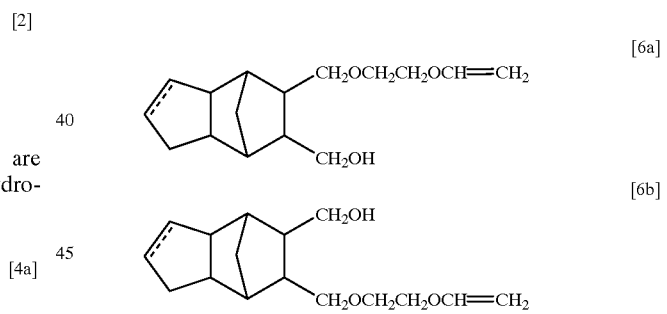

[6a]

[6b]

wherein the dotted line is single bond or double bond.

5. 8,9-bis[(2-vinyloxyethyl)oxymethyl]tricyclo[5.2.1.0$^{2,6}$]decane or 8,9-bis[(2-vinyloxyethyl)oxymethyl]tricyclo[5.2.1.0$^{2,6}$]dece-3-ene according to claim 1, where A$^1$ and A$^2$ in the formula [1] are 2-vinyloxyethyl group shown in the formula [3] below

—CH$_2$CH$_2$OCH=CH$_2$ [3]

as shown in the formula [7] below

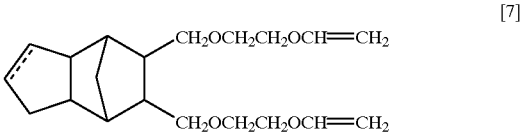

[7]

wherein the dotted line is single bond or double bond.

6. Curable resin composition containing tricyclo[5.2.1.0$^{2,6}$]decane compound or tricyclo[5.2.1.0$^{2,6}$]dece-3-ene compound shown in the formula [1] below

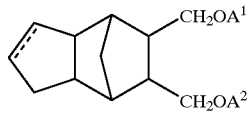

[1]

wherein A$^1$ and A$^2$ are independently hydrogen; or acryloyl group or methacryloyl group shown in the formula [2] below

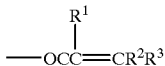

[2]

wherein R$^1$ is hydrogen or C$_1$–C$_4$ alkyl; R$^2$ and R$^3$ are independently hydrogen or C$_1$–C$_{10}$ alkyl; or 2-vinyloxyethyl group shown in the formula [3] below

—CH$_2$CH$_2$OCH=CH$_2$  [3]

wherein the dotted line is single bond or double bond with the proviso that A$^1$ and A$^2$ are not hydrogen at the same time.

* * * * *